United States Patent
Reichow et al.

(10) Patent No.: US 8,317,324 B2
(45) Date of Patent: Nov. 27, 2012

(54) UNITARY VISION AND NEURO-PROCESSING TESTING CENTER

(75) Inventors: Alan W. Reichow, Beaverton, OR (US); Ryan C. Coulter, Portland, OR (US)

(73) Assignee: Nike, Inc., Beaverton, OR (US)

(*) Notice: Subject to any disclaimer, the term of this patent is extended or adjusted under 35 U.S.C. 154(b) by 220 days.

(21) Appl. No.: 12/595,208

(22) PCT Filed: Apr. 14, 2008

(86) PCT No.: PCT/US2008/060249
§ 371 (c)(1),
(2), (4) Date: Mar. 23, 2010

(87) PCT Pub. No.: WO2008/128190
PCT Pub. Date: Oct. 23, 2008

(65) Prior Publication Data
US 2010/0208198 A1   Aug. 19, 2010

Related U.S. Application Data

(60) Provisional application No. 60/941,915, filed on Jun. 4, 2007, provisional application No. 60/923,434, filed on Apr. 13, 2007.

(51) Int. Cl.
*A61B 3/00* (2006.01)
(52) U.S. Cl. ............ 351/203; 351/239; 351/246
(58) Field of Classification Search .......... 351/201, 351/203, 222, 223, 237–239, 246
See application file for complete search history.

(56) References Cited

U.S. PATENT DOCUMENTS

| | | |
|---|---|---|
| 3,861,790 A | 1/1975 | Tamura |
| 4,528,989 A | 7/1985 | Weinblatt |
| 5,050,982 A | 9/1991 | Meissner |

(Continued)

FOREIGN PATENT DOCUMENTS

WO   2000128192   3/2000

(Continued)

OTHER PUBLICATIONS

Cardall, "Contact Lenses in Sport: a General Overview", Optician, Jan. 13, 2006, pp. 22-25, vol. 231, No. 6034, United States.

(Continued)

*Primary Examiner* — Huy K Mai
(74) *Attorney, Agent, or Firm* — Shook, Hardy & Bacon L.L.P.

(57) ABSTRACT

System and methods for testing and/or training a subject's vision and neuro-processing abilities are provided. More specifically, the method may include testing various aspects of the subject's vision and neuro-processing abilities, such as depth perception, anticipation timing, perception speed ability, perception scan ability, etc. By using various tests, an efficient examination may be administered. In accordance with the invention, an individual may be subjected to such a method of testing and/or training at a unitary center capable of presenting such tests to the individual, receiving input from the individual, and processing the received input. Such a unitary test center may further be configurable, so that the tests administered may vary based on the needs of the individual. The received input may then, for example, be used to compute data related to the user's vision and neuro-processing abilities, both overall and for each individual test.

14 Claims, 4 Drawing Sheets

U.S. PATENT DOCUMENTS

| | | | |
|---|---|---|---|
| 5,088,810 | A | 2/1992 | Galanter |
| 5,478,239 | A | 12/1995 | Fuerst et al. |
| 5,812,239 | A | 9/1998 | Eger |
| 5,825,460 | A | 10/1998 | Kohayakawa |
| 5,919,149 | A | 7/1999 | Allum |
| 6,092,058 | A | 7/2000 | Smyth |
| 6,261,239 | B1 | 7/2001 | Abraham-fuchs |
| 6,267,733 | B1 | 7/2001 | Peterson et al. |
| 6,364,845 | B1 | 4/2002 | Duffy et al. |
| 6,371,931 | B1 | 4/2002 | Guillen |
| 6,632,174 | B1 | 10/2003 | Breznitz |
| 6,755,525 | B2 | 6/2004 | Reichow et al. |
| 6,811,258 | B1 | 11/2004 | Grant |
| 6,893,127 | B2 | 5/2005 | Reichow et al. |
| 7,073,208 | B2 | 7/2006 | Penque, Jr. et al. |
| 7,326,060 | B2 * | 2/2008 | Seiller et al. ............. 434/258 |
| 7,849,115 | B2 | 12/2010 | Reiner |
| 2003/0120183 | A1 | 6/2003 | Simmons |
| 2003/0211449 | A1 | 11/2003 | Seiller et al. |
| 2004/0141152 | A1 | 7/2004 | Marino et al. |
| 2005/0053904 | A1 | 3/2005 | Shephard |
| 2005/0273017 | A1 | 12/2005 | Gordon |
| 2006/0195018 | A1 | 8/2006 | Guillen |
| 2006/0244915 | A1 | 11/2006 | Clemons et al. |
| 2006/0251334 | A1 | 11/2006 | Oba et al. |
| 2006/0287617 | A1 | 12/2006 | Taub |
| 2007/0000007 | A1 | 1/2007 | MacDonald |
| 2007/0013870 | A1 * | 1/2007 | Hara et al. ............. 351/237 |
| 2007/0052674 | A1 | 3/2007 | Culver |
| 2007/0254270 | A1 | 11/2007 | Hersh |
| 2008/0003553 | A1 | 1/2008 | Stark et al. |
| 2008/0189173 | A1 | 8/2008 | Bakar et al. |
| 2009/0093305 | A1 | 4/2009 | Okamoto et al. |
| 2009/0129205 | A1 | 5/2009 | Reichow |
| 2009/0130640 | A1 | 5/2009 | Hardy |
| 2009/0150919 | A1 | 6/2009 | Lee |

FOREIGN PATENT DOCUMENTS

| | | |
|---|---|---|
| WO | 2004006747 | 1/2004 |
| WO | 2006088415 | 8/2006 |
| WO | 2007009990 A1 | 1/2007 |
| WO | 2008128192 | 10/2008 |

OTHER PUBLICATIONS

Reichow, et al., "Ultraviolet and Short Wavelength Visible Light Exposure: Why Ultraviolet Protection Alone is Not Adequate", Journal of Long-Term Effects of Medical Implants, 2006, pp. 315-325, vol. 16, No. 4, Begell House, Inc., United States.

Office Action of Jul. 12, 2011 in U.S. Appl. No. 12/595,209.

International Search Report and Written Opinion for PCT/US2010/041564, Mailed Nov. 12, 2010.

International Search Report and Written Opinion for PCT/US08/60229, Mailed September 9, 2008, 9 Pages.

Supplementary European Search Report for EP08745763, Completed June 16, 2010, 9 Pages.

Rouse, et al., "A Comparison Study of Dynamic Visual Acuity Between Athletes and Nonathletes", Journal of the American Optometric Association, Dec. 1988, pp. 946-950, vol. 59, No. 12, United States.

Coffey, et al., "Optometric Evaluation of the Elite Athlete," Problems in Optometry, Mar. 1990, pp. 32-59, vol. 2, No. 1, United States.

Reichow, et al., "Introduction to Behavioral Optometry", Sports Vision, 1993, 75 pages, Optometric Extension Program Foundation, United States.

Reichow, et al., "A Comparison of Contrast Sensitivity in Elite Athletes Versus a Normal Population", American Journal of Optometry and Physiological Optics, Dec. 15, 1986, vol. 63, No. 82, United States.

Farrow, et al., "An Investigation of the Effectiveness of Bolle's Competivision Sport-Glasses on Tennis Performance", Clinical and Experimental Optometry, Jul.-Aug. 2000, pp. 226-231, vol. 83, No. 4.

Herdman, et al., "Computerized Dynamic Visual Acuity Test in the Assessment of Vestibular Deficits", The American Journal of Otology, 1998, pp. 790-796, vol. 19, No. 6, United States.

Tian, et al., "Dynamic Visual Acuity During Transient and Sinusoidal Yaw Rotation in Normal Ulilaterally Vestibulopathic Humans", Experimental Brain Research, Feb. 8, 2001, pp. 12-25, vol. 137, Springer-Verlag, United States.

"Coffey, et al., "Visual Performance Enhancement in Sports Optometry", Sports Vision 1995, pp. 158-177, Butterworth-Heinermann, United States.".

Ferreira, "An Overview of Research in Sports Vision: its History and an Optometric Perspective", The South African Optometrist, Dec. 2003, pp. 142-149, vol. 62, No. 4, Auckland Park, South Africa.

Koenig, "Practicing Perception: Eyes Can Be Trained to be More Effective", USA Today Baseball Weekly, 1996, 3 pages, United States.

International Search Report and Written Opinion for PCT/US08/60249, Mailed Sep. 8, 2008, 9 Pages.

Supplementary European Search Report for EP08745783, Completed June 23, 2010, 10 Pages.

International Search Report and Written Opinion for PCT/US08/60244, Mailed September 4, 2008, 9 Pages.

Supplementary European Search Report for EP08745778.4, Completed June 23, 2010, 9 Pages.

Supplementary European Search Report for EP08780526, Completed June 16, 2010, 11 Pages.

International Search Report and Written Opinion for PCT/US08/60252, Mailed August 15, 2008, 10 Pages.

International Search Report and Written Opinion for PCT/US09/043127, Mailed July 6, 2009, 11 Pages.

Office Action Mailed Apr. 6, 2011 in U.S. Appl. No. 12/595,209, 16 pages.

Office Action of Jan. 6, 2011 in U.S. Appl. No. 12/117,315, 16 pages.

Final Office Action of May 26, 2011 in U.S. Appl. No. 12/117,315, 10 pages.

Final Office Action in U.S. Appl. No. 12/595,209 mailed Jan. 13, 2012.

Office Action in U.S. Appl. No. 12/595,207 mailed Nov. 10, 2011, 19 pages.

Non-Final Office Action in U.S. Appl. No. 12/500,385 mailed Mar. 19, 2012, 39 pages.

Notice of Allowance and Fees Due in U.S. Appl. No. 12/595,207 mailed Apr. 12, 2012, 79 pages.

* cited by examiner

UNITARY VISION AND NEURO-PROCESSING TESTING CENTER

CROSS-REFERENCE TO RELATED APPLICATIONS

This application claims priority to U.S. Provisional Application No. 60/923,434 filed on Apr. 13, 2007, entitled "System and Method for Testing Visual Ability During Simulated Activity," which is hereby incorporated by reference. This application also claims priority to U.S. Provisional Application No. 60/941,915 filed on Jun. 4, 2007, entitled "System and Method for Decoupled Visual Ability Testing," which is hereby incorporated by reference.

STATEMENT REGARDING FEDERALLY SPONSORED RESEARCH OR DEVELOPMENT

Not applicable.

TECHNICAL FIELD

The present invention relates generally to the evaluation and/or training of an individual's vision and neuro-processing abilities.

BACKGROUND OF THE INVENTION

Along with physical ability, an individual's sight plays a role in the individual's performance when participating in an activity, such as a sport. Typically, to improve in the sport or activity, an individual will focus on improving their physical ability to elevate their overall performance. By testing and training the individual's vision and coordination abilities or acuity, however, the individual's performance may also improve.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In accordance with the invention, a method of testing and/or training a subject's vision and coordination abilities is provided. More specifically, the method may include testing various aspects of the subject's vision and coordination ability. By using various tests, a more streamlined examination may be administered. In accordance with the invention, an individual may be subjected to such a method of testing and/or training at a unitary center capable of presenting vision and coordination tests to the individual, receiving input from the individual, and processing the received input. Such a unitary test center may further be configurable, so that the tests administered may vary based on the needs of the individual. The received input may then, for example, be used to compute data related to the user's vision and coordination ability, both overall and for each individual test.

BRIEF DESCRIPTION OF THE DRAWING

The present invention is described in detail below with reference to the attached drawing figures, wherein.

DETAILED DESCRIPTION OF THE INVENTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies.

In accordance with the present invention, systems and methods for testing a subject's vision and coordination abilities at a unitary testing unit are provided. Such a method may include testing various aspects of the subject's vision and coordination abilities (e.g., eye-hand coordination, split attention, reaction time, body coordination, etc.) at a unitary testing unit that may also be capable of processing the resulting data and/or transmitting data over a network to another location for processing. In doing so, the unitary testing center may streamline the process of testing the vision and coordination abilities of subject, and may reduce overhead (e.g., reduce the equipment) needed to perform testing. Additionally, the unitary testing center may be configurable, so that the tests administered may vary based on the needs of the individual. The received input may then, for example, be used to compute results related to the user's vision and coordination abilities, both overall and for each individual test.

In one embodiment, a testing device for testing the vision and coordination ability of a subject is provided. Such a testing device may include a presenting component, an input component, and a processing component, where the presenting component is capable of presenting a test, visual tests, such as a visual tracking test, a distance focusing test, and a visual aiming test, etc. to the subject. In response to each test, the subject may provide input to the testing device. The input component may then be configured to receive the input, and the processing component may be configured to process the received input.

In another embodiment, a method for testing the vision and coordination abilities of a subject, where the method occurs at a unitary location, is provided. The method comprises, in part, administering two or more vision ability tests to the test subject; receiving input from the test subject in response to each test; and processing the input received from the test subject.

Figure 1:
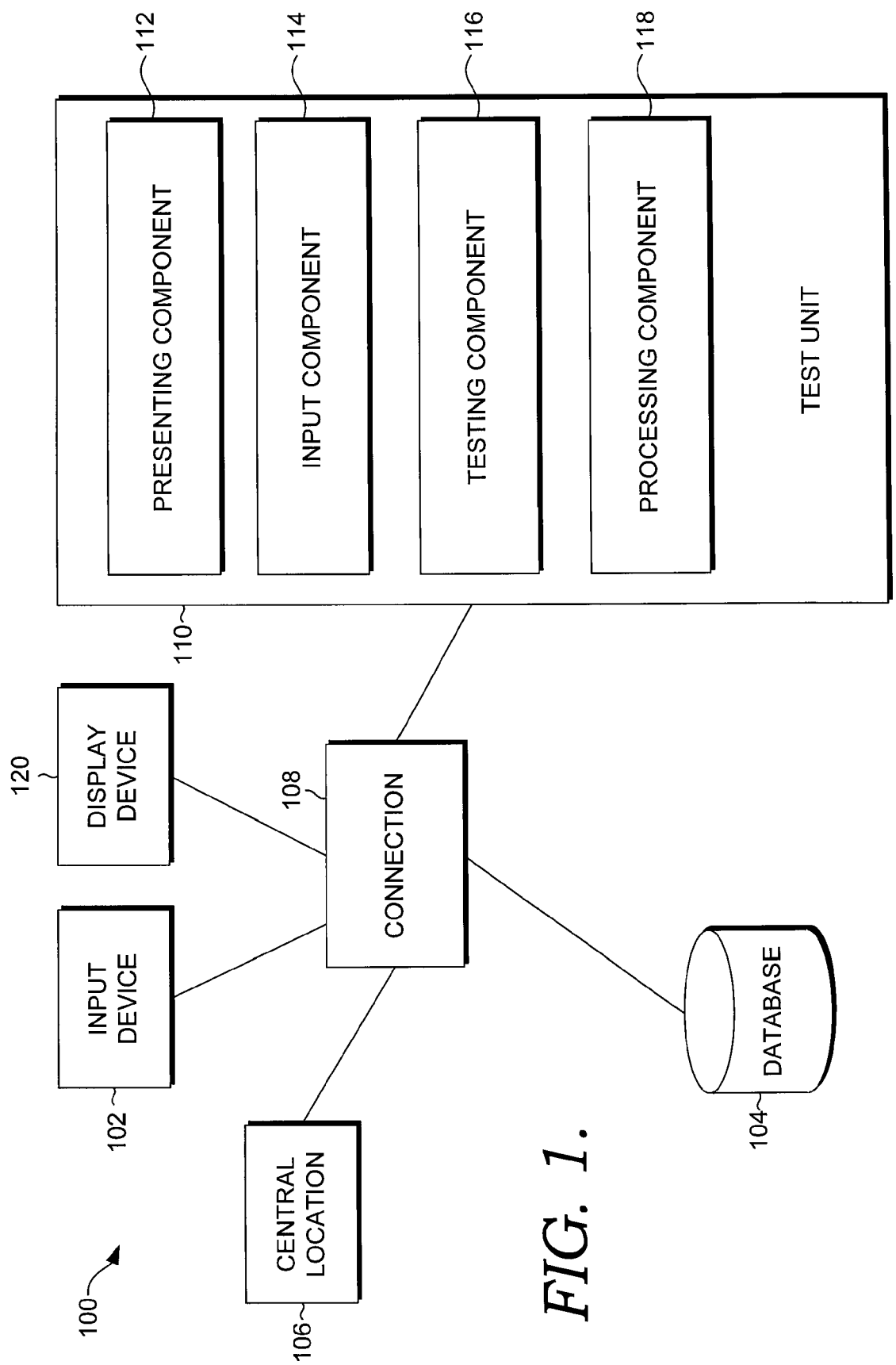
FIG. 1 is a block diagram of a computing system environment suitable for use in implementing the present invention.

Referring to the drawings in general, and initially to FIG. 1 in particular, a block diagram of an exemplary computing system is shown and designated generally as computing system 100 configured to provide for testing the visual and coordination abilities of a subject. It will be understood and appreciated by those of ordinary skill in the art that the computing system 100 shown in FIG. 1 is merely an example of one suitable computing system environment and is not intended to suggest any limitation as to the scope of use or functionality of embodiments of the present invention. Neither should the computing system 100 be interpreted as having any dependency or requirement to any single component or combination of components illustrated therein.

The computing system 100 includes an input device 102, a display device 120, a database 104, a central location 106, and a test unit 110, all in communication with one another via a connection 108. The connection 108 may be made by wire (such as a cable), or wireless (such as a wireless network). Connection 108 may also be a network, where the network may include, without limitation, one or more local area networks (LANs) and/or wide area networks (WANs). Such networking environments are commonplace in enterprise-wide computer networks, intranets, and the Internet. Further, the connection 108 may comprise a locally wired connection between components of computing system 100. Accordingly, the connection 108 is not further described herein.

The input device 102 is capable of receiving one or more responses from a subject. Input device 102 may be any device that may receive responses from a subject. One skilled in the art will appreciate that more than one input device, such as input device 102, may be used with computing system 100. Input device 102 may be, for example, a microphone, joystick, game pad, wireless device, keyboard, keypad, game controller, treadmill, force plate, eye tracking system, gesture recognition system, touch sensitive screen, and/or any other input-initiating component that provides wired or wireless data to the test unit 110, which may be received through the network 108. Input device 102 may include voice recognition equipment and/or software that processes auditory inputs from the test subject. For example, the auditory input from the subject, in order to show recognition of the visual indicia, may be a verbalization of the trait possessed by the visual indicia. In one embodiment, if the trait is a direction orientation of a Landolt "C," the responsive auditory inputs may be "up," "down," "right," and "left." However, one skilled in the art will understand and appreciate that other auditory inputs may be used (e.g., stating a color, numeral, letter, symbol, etc.) to indicate that the subject perceived and/or recognized the visual indicia. It should be noted, however, that the present invention is not limited to implementation on such input devices 102, but may be implemented on any of a variety of different types of devices within the scope of embodiments hereof. Input indicating the subject's response to a displayed visual indicia may be received and captured with input device 102. If the trait is a directional orientation, a satisfactory test response may be identifying the direction that the visual indicia is facing. By way of example only, without limitation, identifying may include the subject providing input by manipulating a joystick in a direction corresponding to the directional orientation on a hand-held device employed as the input device 102.

The display device 120 may be capable of displaying output video visually observable by a subject and may be any type of computer, testing apparatus, or television monitor, including cathode ray tube, liquid crystal display, plasma screen, or any other display type, or may comprise a screen upon which images are projected, either from the front or from the rear. Further, the display device 120 may provide a user interface for a test administrator to interact with the test unit 110 before, during, and after administering the vision ability tests to a test subject.

If input device 102 is an eye tracking system, the position and/or focus of the eyes of subject may be monitored and an input registered when the eyes are positioned and/or focused at the proper location.

If input device 102 is a gesture recognition system, a variety of systems and/or methods may be used to receive inputs. For example, one or more cameras may be used to monitor the movement of a subject's body limbs and/or extremities and, in conjunction with appropriate hardware and/or software, register an input when subject makes an appropriate gesture. Gesture recognition systems may also utilize optical markers attached to subject to facilitate motion tracking. Transmitters attached to subject and receivers (for example, utilizing radio infrared, sonic, subsonic, or ultrasonic transmissions) may also be utilized as part of a gesture recognition system.

If input device 102 is a touch sensitive screen, any type of touch sensitive screen may be utilized. Also, an overlay of a touch sensitive material may be used to receive touch inputs in conjunction with a display that is not itself touch sensitive. Such an overlay may be any distance from the display.

The test unit 110, as shown in FIG. 1, may be any type of computing device, embodiments of which will be more fully discussed below with reference to FIGS. 4 and 5. The database 104 may be configured to store information associated with tests of vision and coordination abilities. It will be understood and appreciated by those of ordinary skill in the art that the information stored in the database 104 may be configurable and may include any information relevant to the testing of vision and coordination abilities. The content and volume of such information are not intended to limit the scope of embodiments of the present invention in any way. Although illustrated as a single, independent component, database 104 may, in fact, be a plurality of database, for instance, a database cluster. Further, portions or the entirety of the database 104 may reside on a computing device associated with the test unit 110, another external computing device (not shown), and/or any combination thereof. One skilled in the art should appreciate that database 104 is optional and need not be implemented in conjunction with the computing system 100.

Returning to FIG. 1, the test unit 110 may include a presenting component 112, an input component 114, a testing component 116, and a processing component 118, shown in accordance with an embodiment of the present invention. It will be understood by those of ordinary skill in the art that the components 112, 114, 116, and 118 illustrated in FIG. 1 are exemplary in nature and in number, and should not be construed as limiting. Any number of components may be employed to achieve the desired functionality within the scope of embodiments of the present invention.

The presenting component 112 may be capable of displaying output video visually observable by a subject and may be any type of computer, testing apparatus, or television monitor, including cathode ray tube, liquid crystal display, plasma screen, or any other display type, or may comprise a screen upon which images are projected, either from the front or from the rear.

In one embodiment, presenting component 112 may be an apparatus that uses mirror and/or lenses strategically placed to generate a visual perspective of distance within a limited spatial area (e.g., providing a periphery configuration of mirrors to produce a tunnel effect). An example of such an apparatus is a perspective testing apparatus utilizing mirrors to generate a perspective of distance. Such an apparatus may include a mirror that displays the visual indicia in a central foveal area (i.e., directly in front of the subject), and may further include side mirrors that display a visual indicia to test peripheral visual ability.

In another embodiment, an apparatus may include lenses that change perceived distance and/or size of the displayed visual indicia to achieve a simulated distance. As a result, such an apparatus may provide a displayed visual indicia that appears to the test subject to be nearer or farther than the actual display. Thus, this configuration creates the perspective of optical infinity to the test subject.

One skilled in the art will appreciate that presenting component 112 may comprise multiple devices that, in combination, display some of the visual stimuli typical for a particular activity. In one embodiment, a single device may be used to display multiple displays of visual indicia (e.g., split-screen).

Presenting component 112 may alternatively comprise display glasses, goggles, visors, and the like, that may be worn by a subject to provide a visual display for the subject that is not typically visible to others. Additionally, presenting component 112 may provide a two dimensional or three dimensional image to the test subject. The three dimensional image display may include virtual reality or holographic presentations to the subject.

In operation, the presenting component 112 may be configured to present one or more visual indicia to a test subject. As discussed more fully below, presenting component 112 may present visual indicia in varying ways to test different aspects of the subject's vision and coordination abilities. In general, each of the visual indicia may possess a trait or traits. This trait may be, for example, a directional orientation (e.g., arrow, Landolt "C", Tumbling E, etc.), a position on a user interface (e.g., located in a particular quadrant of the display), one of a predetermined number of mutually exclusive traits (e.g., indicator that faces either up, down, left, or right), or any combination of traits. Further, one of ordinary skill in the art will understand and appreciate that other traits may be used, and the present invention is not limited to any particular trait.

The input component 114 may be configured to receive input from the test subject (e.g., by utilizing input device 102). Any suitable receiving component that is capable of receiving input provided by the subject may be used in accordance with this invention. By way of example, without limitation, the subject may provide input utilizing a keyboard, joystick, trackball, or the like. The input may depend upon the presenting component. For example, if the presenting component is touch-sensitive, the subject could provide input by touching the presenting component. In another embodiment, the input component could have voice recognition capability, where the subject may provide input with a vocalized response that is recognized by the input component. One skilled in the art will understand and appreciate that any suitable input component may be used in accordance with the present invention. Certain types may be preferred based on the tests presented by the presenting component and, as discussed above, the capabilities of the presenting component. After receiving input from the subject, the input component 114 may store the input, for instance, in database 104 for future reference.

The testing component 116 is configured to provide tests to the subject. As will be discussed more fully below with respect to FIG. 2, testing component 116 may provide two or more tests to determine the vision and coordination abilities of a subject. More specifically, multiple tests may be provided at a unitary location, such as test unit 110. Further, testing component 116 is configurable so that the tests may vary depending on the subject. For example, the tests may vary given the test subject's particularized sport or activity, competition level, visual strengths/weaknesses, etc. Thus, the testing component 116 may also be responsible for determining the tests (and level or difficulty of tests) presented by the presenting component 112.

Figure 3:
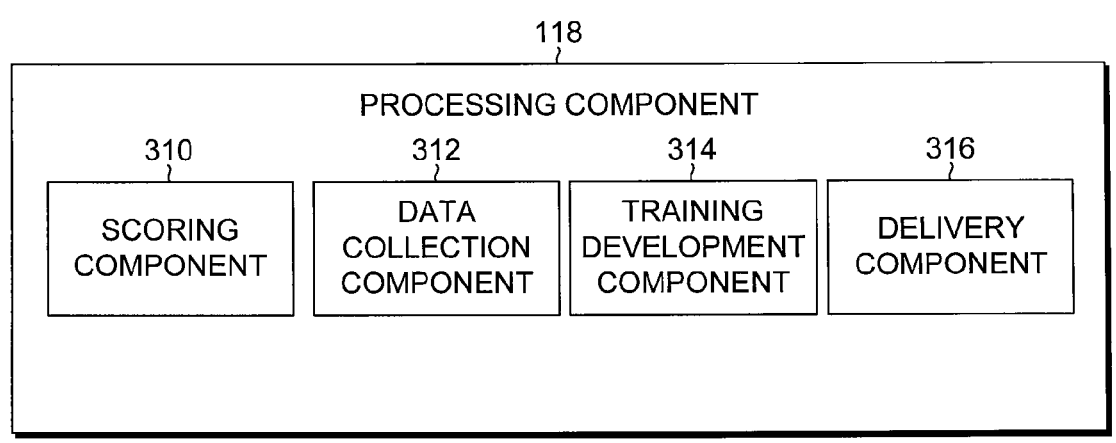
FIG. 3 illustrates a block diagram of an exemplary processing component for use in implementing the present invention.

The processing component 118 is provided to process the input received by input component 114. As shown in FIG. 3, the processing component 118 may comprise a scoring component 310, a data collection component 312, a training development component 314, and a delivery component 316. The scoring component 310 may be configured to utilize a scoring algorithm to derive a score based on the subject's response to the tests presented. The subject's responses may be determined by comparing such response to those from a particular population, typically retrieved from the database 104. The scoring component 310 may provide an evaluation of the vision and coordination abilities of the subject incident to receiving and measuring one or more responses to the visual indicia. Once a score (e.g., percentile) is determined, it may be presented to the subject via presenting component 112. The score may be presented at the conclusion of each test, at the conclusion of all tests, or a combination thereof.

The data collection component 312 is configured to collect the data received from input component 114. Such data may then be stored, for example, in database 104. The data collected may further be used to create standards for a particular population, which may then be used by scoring component 310. One of skill in the art will appreciate that database 104 and/or scoring component 310 may be located remotely from other components of system 100.

The training development component 314 is configured to develop a training plan or regimen for the test subject based on the collected data and determined scores. In embodiments of the present invention, test unit 110 may be used for training the test subject, after the subject has undergone testing.

The delivery component 316 is configured to transmit the determined score, collected data, and the like to presenting component 112. The delivery component 316 may additionally provide this data to an external computing device, such as central location 106, for further consideration, analysis, or storage. In one embodiment, the delivery component 316 may provide data in real time to testing component 116, such that the tests may be configured or varied while still in the testing process. It should be understood and appreciated by those of ordinary skill in the art that, although embodiments and examples are discussed above, the delivery component 316 may provide information related to testing vision and coordination abilities to any component of the computing system 100, both internal and external to the test unit 110.

One skilled in the art will appreciate that the delivery component 316 may send information from test unit 110 at any desired frequency. That is, the information may be sent to a desired location, for example, after a subject completes all tests or, alternatively, after each individual test. If sending the information to central location 106 or database 104 for storage and/or processing, the information may be sent collectively for all subjects at the end of the day. The frequency may depend upon the storage capacity and processing capability of the test unit 110, as well as the desired use of the information.

Figure 2:
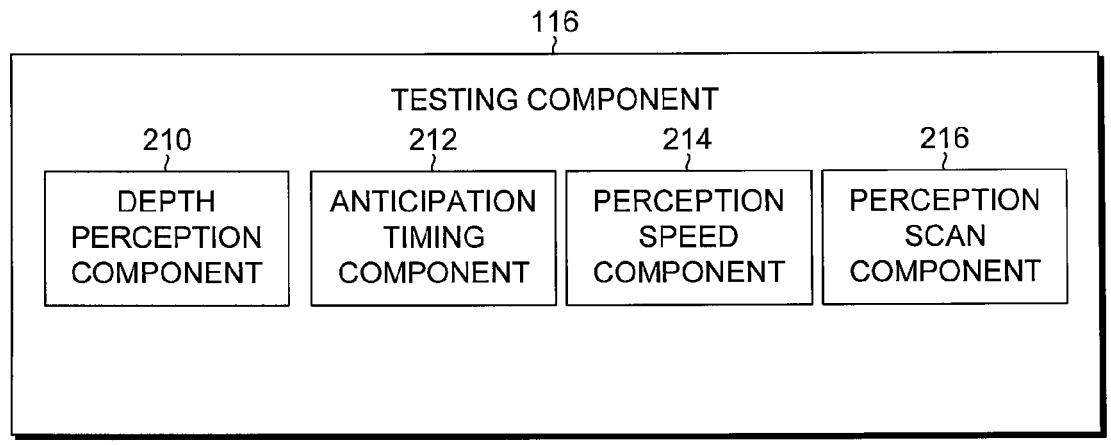
FIG. 2 illustrates a block diagram of an exemplary testing component for use in accordance with an embodiment of the present invention.

Referring now to FIG. 2, testing component 116 is further illustrated. Testing component 116 may comprise a depth perception coordination component 210, an anticipation timing component 212, a scan perception component 214, and a speed perception component 216. Each of these components may be used by test unit 110 to test various aspects of an individual's vision and coordination abilities. One skilled in the art will appreciate that other tests may be used and are within the scope of the invention.

The depth perception component 210 is configured to test the depth perception of a subject, and may include displaying a visual indicia at different depths and requiring the test subject to locate the visual indicia that is or appears to be at a specified depth. In one embodiment, a plurality of visual indicia may be presented, where each visual indicia appears at the same depth except for one. In such an embodiment, the test subject may locate the visual indicia that appears at a different depth from the other indicia, and this response is inputted into the test unit 110. One skilled in the art will appreciate and understand that any suitable test that tests a subject's depth perception may be used by the depth perception component 210.

The anticipation timing component 212 is configured to test the ability of a test subject to anticipate the timing of a visual indicia where the visual indicia is in motion. In one embodiment, a visual indicia, such as a dot or circle, is presented to a subject, whereby the indicia appears to be in motion towards the subject. The subject may then provide an input representing when the subject anticipates the visual indicia reaching a specified position. One skilled in the art will appreciate and understand that any suitable test of depth perception may be used by the depth perception component 212.

The scan perception component 214 is configured to test the ability of a test subject to visually scan. Any suitable test may be used and is within the scope of this invention. By way of example, without limitation, a visual indicia may be presented to the test subject. The visual indicia may include a grid of singular visual indicia in a specified pattern. For example, a grid of dots may be displayed where some dots are solid and others are not. The solid dots may then appear as an outline, similar to the other dots on the grid, and the subject must identify those dots that were previously solid. Another exemplary scan perception test may include presenting a random set of numbers for a specified time to the subject, and having the subject input the perceived numbers.

The speed perception component 216 is configured to test the speed with which a subject is able to perceive a visual indicia. In one embodiment, a visual indicia is displayed or flashed to the test subject for a specified period of time. Another visual indicia is then displayed for varying time periods in different locations on the display device. Between each flashed visual indicia, a neutral visual indicia may be presented in the center of the display. Having the test subject identify each of the flashed visual indicia measures their visual and neuro-processing ability to perceive at specified speeds. One skilled the art will appreciate that any suitable test that tests visual speed perception may be used.

Figure 4:
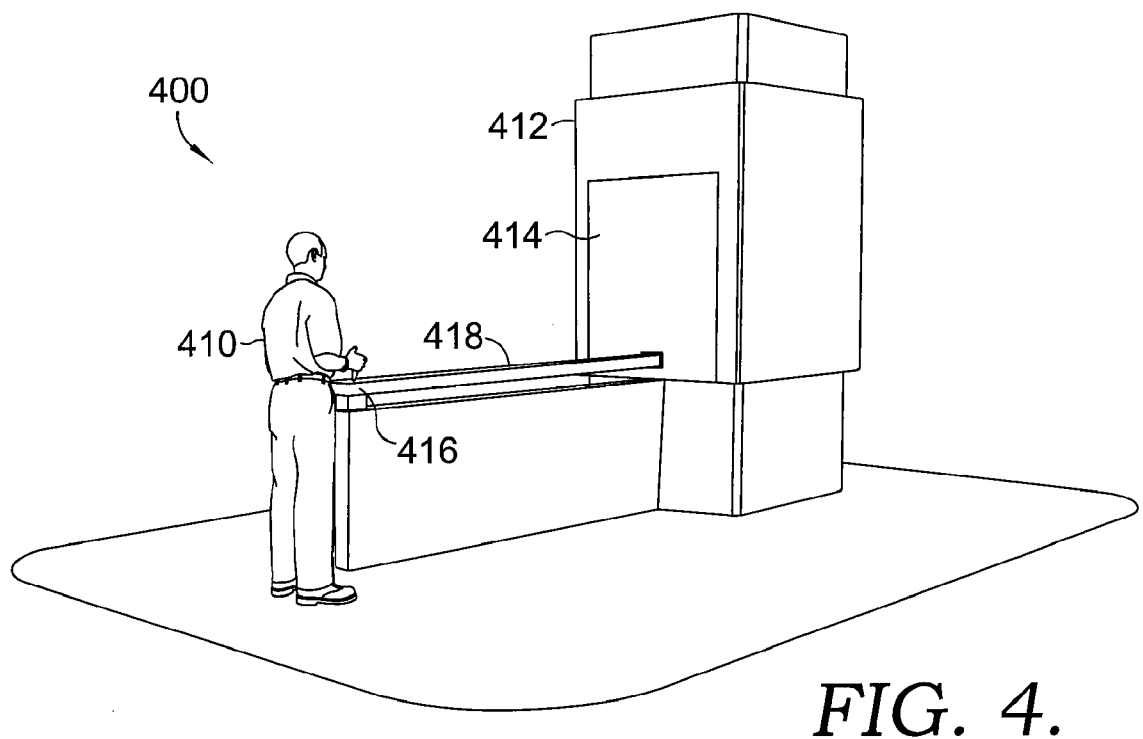
FIG. 4 illustrates an exemplary unitary vision and coordination testing unit, in accordance with an embodiment of the present invention.

Referring now to FIG. 4, an exemplary vision and neuro-processing testing system 400 is illustrated, in accordance with an embodiment of the present invention. By having a unitary test unit, such as test unit 412, that is capable of presenting several tests to a subject, a better overall evaluation of the subject's vision and neuro-processing abilities may be provided. Further, because test unit 412 may include processing capabilities, it is able to process the data, resulting in a determined score and/or a training regimen for the subject. Display 414 may output visual stimuli to subject 410. Subject 410 may provide inputs to visual stimuli using input device 416. Spatial display 418 may alternatively and/or additionally output visual stimuli. Spatial display 418 may, for example, be used in conjunction with speed perception component 216, anticipation timing component 212, or other test components, as described above. Of course, spatial display 418 may be used in conjunction with any other type of vision test.

Figure 5:
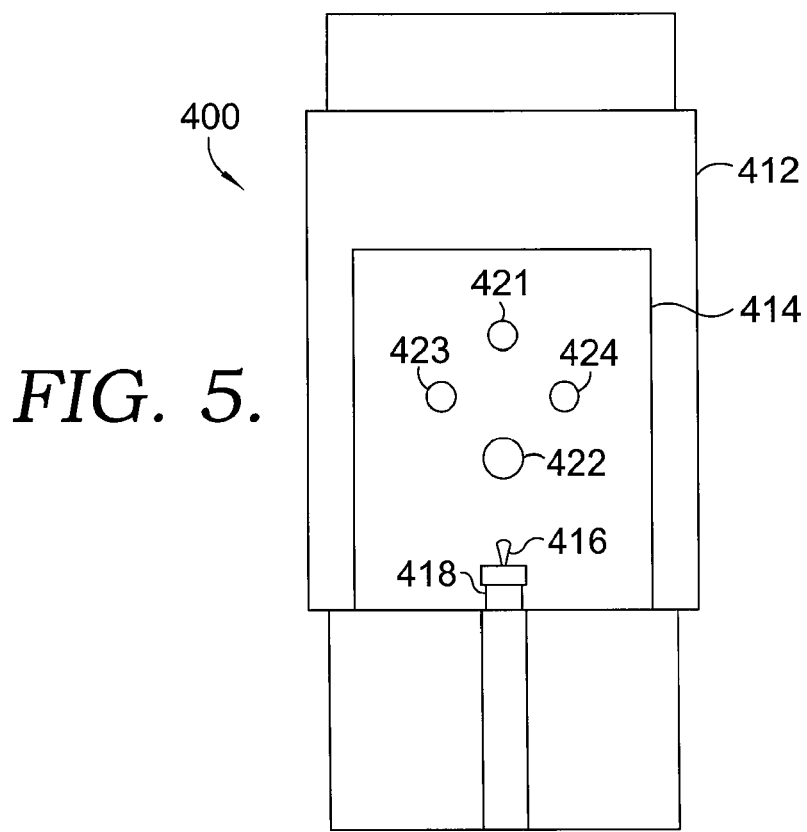
FIG. 5 illustrates another embodiment of a unitary vision and coordination testing unit, in accordance with the present invention.

FIG. 5 further illustrates a vision and neuro-processing testing system 400, in accordance with an embodiment of the present invention. More specifically, display 414 outputs visual stimuli in this example a top indicia 421, a bottom indicia 422, a left indicia 423, and a right indicia 424. Indicia displayed on display 414 may be static or moving. Subject may input the selection of one or more indicia using input device 416. The indicia selected may be based upon criteria such as motion, alignments, depth, color, size, contrast, or any other visual property.

Figure 6:
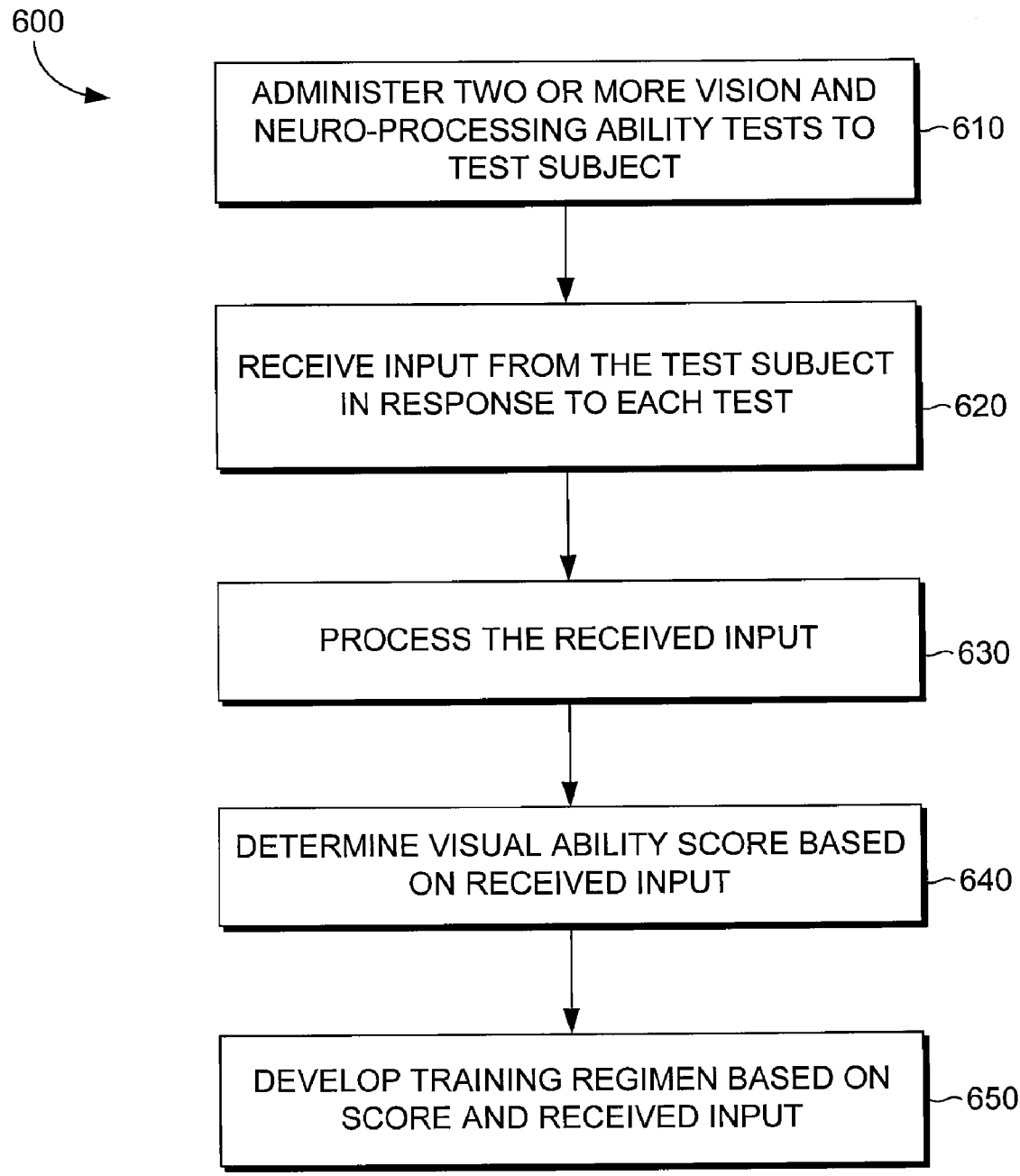
FIG. 6 illustrates a flow diagram showing a method for testing the vision and coordination abilities of a subject at a unitary location, in accordance with an embodiment of the present invention.

FIG. 6, a flow diagram 600 is illustrated that shows a method of testing the vision and neuro-processing abilities of a subject. Although the terms "step" and "block" are used hereinbelow to connote different elements of methods employed, the terms should not be interpreted as implying any particular order among or between various steps herein disclosed unless and except when the order of individual steps is explicitly described. Initially, two or more vision and/or neuro-processing tests are administered to a test subject (e.g., utilizing test unit 110 of FIG. 1). This is indicated at block 610. One skilled in the art will appreciate that any of the tests described above may be administered, as well as any other test that measures an individual's vision and neuro-processing abilities. The specific tests administered and the order of the tests may be configured on the subject's ability level, competition level, particular activity, and the like. While the test is administered to the subject, the subject may provide the appropriate response by interacting with an input device that is connected to the test unit via an input component. This is indicated at block 620. Multiple input devices may be used, and more than one input may be received from the subject. For example, during a split attention test, a subject may provide one response to a visual indicia testing eye-hand coordination, while the subject may provide another response to a visual indicia at a separate location, as described above. A processing component (e.g., processing component 118 in FIG. 1) may then process the received input by, for example, collecting the data, determining a score, or developing a training regimen. The data may be stored, for example, in database 104, or sent via a delivery component to, for example, central location 106. This is indicated at block 630.

Optionally, at block 640, the data received from the subject's input with each test may be used to determine a score for the subject. An individual score may be determined for each test, and an overall score may be determined based on the data from all tests. The score may further be based on corresponding data for a particular population, and the subject's score may be compared accordingly (e.g., the subject may be given a percentile of their performance). At block 650, a training regimen may be developed for the test subject to train his or her vision and coordination abilities based on, for example, their determined score and their received input in response to the vision ability tests.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and sub-combinations are of utility and may be employed without reference to other features and sub-combinations. This is contemplated by and is within the scope of the claims.

What is claimed is:

1. A device for testing the visual and neuro-processing ability of a subject comprising:
   a presenting component configured to present two or more vision and neuro-processing ability tests, wherein a vision and neuro-processing ability test includes a test that measures both the vision and neuro-processing of a subject, the two or more vision and neuro-processing ability tests comprise at least one selected from the following:
   an anticipation test, the anticipation test comprises:
      a visual indicia in motion presented to the test subject; and
      an input received from the test subject in response to the visual indicia in motion, wherein the input received from the test subject represents when the subject anticipates the visual indicia will reach a specified location;
   a scan perception test, the scan perception test comprises:
      a plurality of first visual indicia presented to the test subject, wherein a subset of first visual indicia in the plurality of first visual indicia share a specified characteristic;
      a plurality of second visual indicia subsequently presented to the test subject, wherein each of the plurality of second visual indicia is an outline of each of the plurality of the first visual indicia; and
      one or more inputs received from the test subject corresponding to a location of each of the subset of first visual that share the specified characteristic;
   a speed perception test, the speed perception test comprises:
      a plurality of third visual indicia presented to the test subject for a specified period of time at a first location;
      a plurality of fourth visual indicia presented to the test subject for varying time periods at a plurality of different locations; and
      a plurality of inputs received from the test subject in response to each of the plurality of third visual indicia and each of the plurality of fourth visual indicia;
   an input component configured to receive the input provided by the subject; and
   a processing component configured to process the received input.

2. The device of claim 1, wherein the processing component comprises a scoring component that determines a score based on the received input.

3. The device of claim 2, wherein the processing component further comprises a training development component that provides a training regimen based on the score.

4. The device of claim 1, wherein one of the two or more vision and neuro-processing ability tests comprises a depth perception test.

5. The device of claim 4, wherein the depth perception test comprises a fifth visual indicia presented to the subject and a fifth input received from the subject locating the fifth visual indicia in response to a fifth location of the fifth visual indicia.

6. The device of claim 1, wherein one of the two or more vision and neuro-processing ability tests comprises a split attention test, the split attention test comprises a sixth visual indicia presented to the subject at a sixth location that the subject provides, as a sixth input using a first input device, a response locating the sixth visual indicia and a seventh visual indicia presented to the subject at a seventh location that requires a response from the subject using a second input device, different from the first input device.

7. The device of claim 6, wherein the seventh visual indicia is a Landolt C.

8. A method of testing the vision and neuro-processing ability of a test subject, wherein the method occurs at a unitary location, the method comprising:
   administering two or more vision and neuro-processing ability tests to a test subject, wherein a vision and neuro-processing ability test is a test that measures both the vision and neuro-processing ability of a subject, wherein the two or more vision and neuro-processing ability tests comprise at least one selected from the following:
   an anticipation test, the anticipation test comprises:
      a visual indicia in motion presented to the test subject; and
      an input received from the test subject in response to the visual indicia in motion, wherein the input received from the test subject represents when the subject anticipates the visual indicia will reach a specified location;
   a scan perception test, the scan perception test comprises:
      a plurality of first visual indicia presented to the test subject, wherein a subset of first visual indicia in the plurality of first visual indicia share a specified characteristic;
      a plurality of second visual indicia subsequently presented to the test subject, wherein each of the plurality of second visual indicia is an outline of each of the plurality of the first visual indicia; and
      one or more inputs received from the test subject corresponding to a location of each of the subset of first visual that share the specified characteristic;
   a speed perception test, the speed perception test comprises:
      a plurality of third visual indicia presented to the test subject for a specified period of time at a first location;
      a plurality of fourth visual indicia presented to the test subject for varying time periods at a plurality of different locations; and
      a plurality of inputs received from the test subject in response to each of the plurality of third visual indicia and each of the plurality of fourth visual indicia;
   receiving input from the test subject in response to each test; and
   processing the received input.

9. The method of claim 8, wherein the method further comprises determining a score based on the received input.

10. The method of claim 9, wherein the method further comprises providing a training regimen based on the score.

11. The method of claim 8, wherein one of the two or more vision and neuro-processing ability tests comprises a depth perception test.

12. The method of claim 8, wherein one of the two or more vision and neuro-proces sing ability tests comprises an eye-hand coordination test, the eye-hand coordination test comprising:
   a fifth visual indicia presented to the test subject at a second location; and a second input received from the test subject locating the fifth visual indicia in response to the second location of the fifth visual indicia.

13. The method of claim 8, wherein one of the two or more vision and neuro-processing ability tests comprises a split attention test, the split attention test comprising:
   a sixth visual indicia presented to the test subject at a third location, a third input received from the test subject in response to the sixth visual indicia, the test subject using a first input device, and
   a seventh visual indicia presented to the test subject at a seventh location, a second input received from the test subject in response to the seventh visual indicia, the test subject using a third input device.

14. The method of claim 13, wherein the seventh visual indicia is a Landolt C.

\* \* \* \* \*